(12) United States Patent
Lai

(10) Patent No.: US 6,765,267 B2
(45) Date of Patent: Jul. 20, 2004

(54) PIXEL STRUCTURE

(75) Inventor: Han-Chung Lai, Taoyuan Hsien (TW)

(73) Assignee: Au Optronics Corporation, Hsinchu (TW)

( * ) Notice: Subject to any disclaimer, the term of this patent is extended or adjusted under 35 U.S.C. 154(b) by 0 days.

(21) Appl. No.: 10/248,413

(22) Filed: Jan. 17, 2003

(65) Prior Publication Data

US 2003/0146475 A1 Aug. 7, 2003

(30) Foreign Application Priority Data

Feb. 6, 2002 (TW) .................................. 91102059 A (51) Int. Cl.[7] .......................................... H01L 29/788
(52) U.S. Cl. ........................ 257/359; 257/316; 257/797; 349/5; 349/95; 349/187; 349/7; 349/8
(58) Field of Search ............................ 257/359, 316, 257/797; 349/5, 95, 187, 7, 8

(56) References Cited

U.S. PATENT DOCUMENTS 5,936,695 A * 8/1999 Hida et al. .................. 349/153
6,136,632 A * 10/2000 Higashi ....................... 438/166
6,204,895 B1 * 3/2001 Nakamura et al. ............. 349/5

FOREIGN PATENT DOCUMENTS

JP 2002221735 * 1/2001 ......... G02F/1/1368

* cited by examiner

Primary Examiner—Nathan J. Flynn
Assistant Examiner—Fazli Erdem
(74) Attorney, Agent, or Firm—Jiang Chyun IP Office (57) ABSTRACT

A pixel structure comprising a thin film transistor, a pixel electrode, a scan line, a data line and an alignment mark. The alignment mark is formed beneath the data line. Misalignment is assessed through the degree of shifting between the alignment mark and the data line relative to each other. In addition, misalignment is also gauged through the degree of shifting between the alignment mark and the channel layer within the thin film transistor relative to each other.

12 Claims, 7 Drawing Sheets

PIXEL STRUCTURE

CROSS REFERENCE TO RELATED APPLICATIONS

This application claims the priority benefit of Taiwan application serial no. 91102059, filed Feb. 6, 2002.

BACKGROUND OF INVENTION

1. Field of Invention

The present invention relates to a pixel structure. More particularly, the present invention relates to a pixel structure having a data line with an alignment mark underneath.

2. Description of Related Art

The rapid progress in multi-media communication is largely a consequence of technological advances in the manufacturing of semiconductor and display devices. In the past, cathode ray tubes (CRTs) are the principle types of display devices in the market due to stable quality and relative low cost. However, bulkiness, weight and power consumption restricts the CRT to a desktop terminal/display type of environment. In recent years, thin film transistor liquid crystal display (TFT-LCD) has gradually replaced CRT as a dominant display device. A TFT-LCD not only provides high-quality picture image and uses very little power, the display device is light, compact and radiation free as well.

Figure 1:
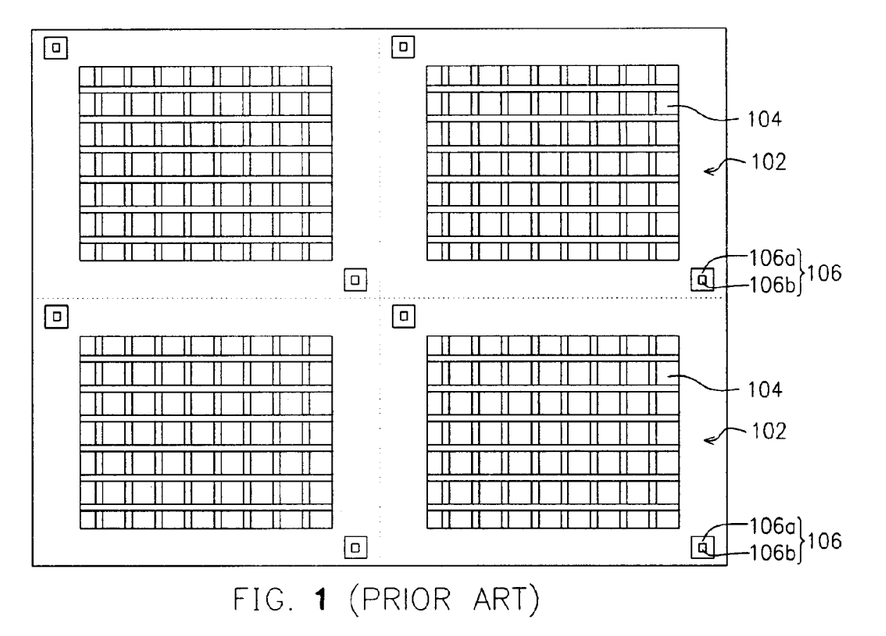
FIG. 1 is a schematic top view of a conventional thin film transistor array having an alignment mark thereon.

FIG. 1 is a schematic top view of a conventional thin film transistor array having an alignment mark thereon. In general, a thin film transistor array is formed on a sheet of transparent substrate 100. The transparent substrate 100 is divided into a plurality of blocks 102. Each block 102 includes a pixel array 104. Each pixel array 104 comprises a plurality of pixels with each pixel falling on a pixel point ordered into an array. In addition, a pair of alignment marks 106 is formed on the opposite corner of the pixel array 104 in each block 102. Each alignment mark 104 is constructed from a first metallic layer 106a and a second metallic layer 106b stacking on top of the first metallic layer 106a.

Figure 2:
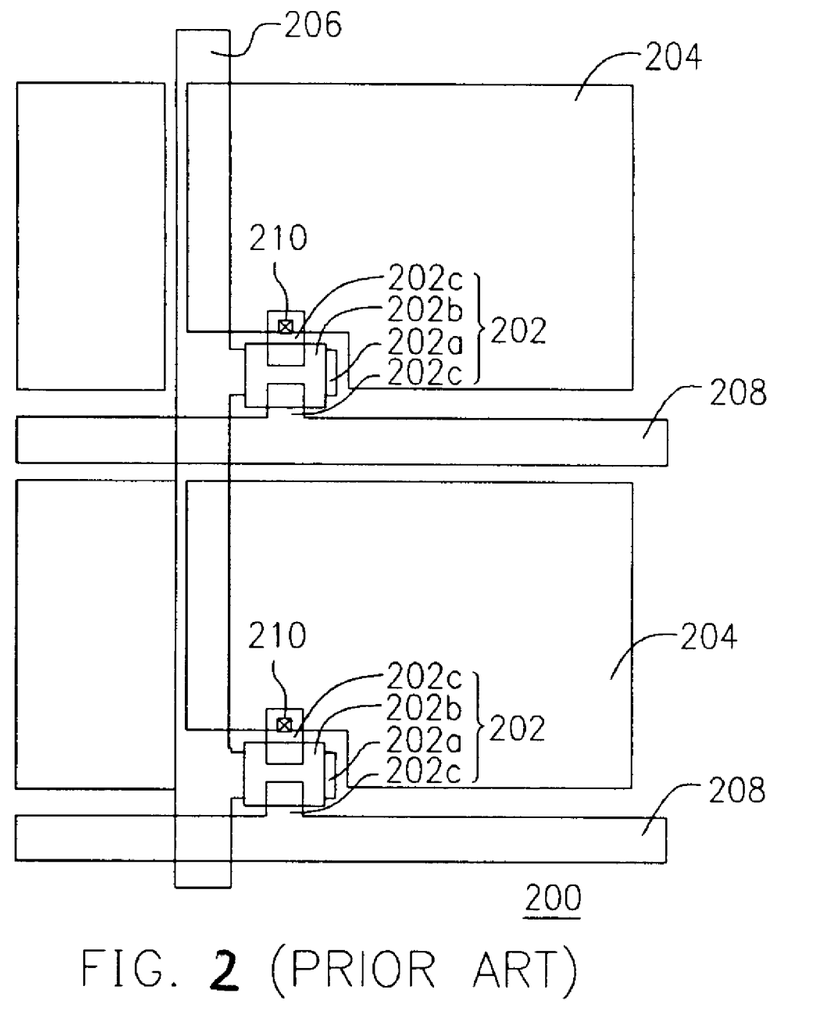
FIG. 2 is a schematic top view of a conventional pixel structure.

FIG. 2 is a schematic top view of a conventional pixel structure. As shown in FIG. 2, pixel units are normally formed over a transparent substrate 200. Each pixel unit comprises of a thin film transistor 202, a pixel electrode 204 corresponding to the thin film transistor 202, a scan line 206 and a data line 208. The thin film transistor 202 further comprises a gate electrode 202a, a channel layer 202b and source/drain terminals 202c. The scan line 206 and the gate electrode 202a of the thin film transistor 202 are electrically connected. The pixel electrode 204 and the data line 208 are electrically connected to the respective source/drain terminals 202c.

As shown in FIG. 2, the fabrication of an array of pixel units 200 involves many steps. Such steps include forming the gate electrode 202a and the scan line 206, the channel layer 202b, the source/drain terminals 202c and the data line 208, the source/drain (S/D) contact 210 and the pixel electrode 204. Hence, the alignment of photomask in each step is critical. Any mis-alignment of the photomask may lead to a shift in position of the channel layer 202b within the thin film transistor 202 or a non-symmetrical layout of the source drain terminals 202c on each side of the channel layer 202b.

The first metallic layer 106a and the gate electrode 202a of the thin film transistor 202 are formed using the same photomask. Similarly, the second metallic layer 106b and the source/drain terminals 202c of the thin film transistor 202 are formed using the same photomask. Hence, by observing the relative stacking position of the first metallic layer 106a and the second metallic layer 106b, any mis-alignment between the two photomasks can be determined and non-symmetrical distribution of the source/drain terminals 202c on each side of the channel layer 202b can be prevented. Since the alignment mark 106 only points to any alignment problems between the gate electrode 202a and the source/drain terminals 202c, the alignment mark 106 is unable to prevent any incorrect positioning of the channel layer 202b.

SUMMARY OF INVENTION

Accordingly, one object of the present invention is to provide a pixel structure that provides a better alignment between the source/drain terminal and the gate electrode within each pixel unit.

To achieve these and other advantages and in accordance with the purpose of the invention, as embodied and broadly described herein, the invention provides a pixel structure on a transparent substrate. The pixel structure mainly includes a first conductive layer, a first dielectric layer, a channel layer, a second conductive layer, a second dielectric layer and a pixel electrode. The first conductive layer is formed over the transparent substrate. The first conductive layer further includes a scan line, a gate electrode and an alignment mark. The first dielectric layer is formed over the transparent substrate and covers the first conductive layer. The channel layer is formed over the first dielectric layer above the gate electrode. The second conductive layer is formed over the first dielectric layer. The second conductive layer further includes a data line and a source/drain terminal. The second dielectric layer is formed over the first dielectric layer and covers the second conductive layer. The pixel electrode is formed over the second dielectric layer. The alignment mark is formed beneath the data line.

According to this invention, the gate electrode, the channel layer and the source/drain terminals together constitute a thin film transistor. In addition, the gate electrode connects electrically with the scan line. Similarly, the pixel electrode and the data line connect electrically with the source/drain terminals. The scan line extends in a direction perpendicular to the data line. The alignment mark has a longitudinal profile and extends in a direction parallel to the data line. Furthermore, width of the alignment mark is equal to or smaller than the data line.

This invention also provides a thin film transistor array that includes a transparent substrate, a first conductive layer, a first dielectric layer, a plurality of channel layers, a second conductive layer, a second dielectric layer and a plurality of pixel electrodes. The first conductive layer is formed over the transparent substrate. The first conductive layer further includes a plurality of scan lines, a plurality of gate electrodes and a plurality of alignment marks. The first dielectric layer is formed over the transparent substrate covering the first conductive layer. The channel layers are formed on the first dielectric layer above various gate electrodes. The second conductive layer is formed over the first dielectric layer. The second conductive layer further includes a plurality of data lines and a plurality of source/drain terminals. The second dielectric layer is formed over the first dielectric layer covering the second conductive layer. The pixel electrodes are formed over the second dielectric layer. The alignment marks are positioned beneath the data lines.

According to this invention, the gate electrodes, the channel layers and the source/drain terminals together constitute a thin film transistor array. In addition, each gate electrode connects electrically with a corresponding scan line. Similarly, each set of pixel electrode and data line connects electrically with a corresponding pair of source/drain terminals. The scan lines extend in a direction perpendicular to the data lines. The alignment marks have a longitudinal profile and extend in a direction parallel to the data lines. Furthermore, width of the alignment marks is equal to or smaller than the data lines.

It is to be understood that both the foregoing general description and the following detailed description are exemplary, and are intended to provide further explanation of the invention as claimed.

BRIEF DESCRIPTION OF DRAWINGS

The accompanying drawings are included to provide a further understanding of the invention, and are incorporated in and constitute a part of this specification. The drawings illustrate embodiments of the invention and, together with the description, serve to explain the principles of the invention. In the drawings.

DETAILED DESCRIPTION

Reference will now be made in detail to the present preferred embodiments of the invention, examples of which are illustrated in the accompanying drawings. Wherever possible, the same reference numbers are used in the drawings and the description to refer to the same or like parts.

Figure 3:
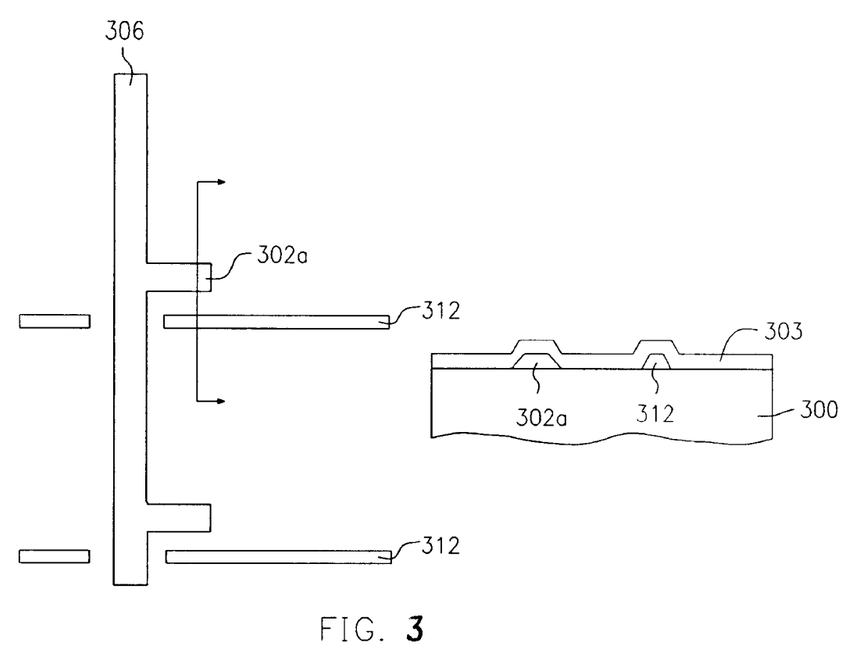
FIGS. 3 through 6 are schematic top and a cross-sectional views showing the progression of steps for producing a pixel structure according to one preferred embodiment of this invention.

FIGS. 3 through 6 are schematic top and a cross-sectional views showing the progression of steps for producing a pixel structure according to one preferred embodiment of this invention. As shown in FIG. 3, a first conductive layer is formed over a transparent substrate 300. The first conductive layer mainly comprises a scan line 306, a gate electrode 302a and an alignment mark 312. The gate electrode 302a connects electrically with the scan line 306. The alignment mark 312 has a longitudinal profile. After forming the scan line 306, the gate electrode 302a and the alignment mark 312, a first dielectric layer 303 is formed over the transparent substrate 300. The first dielectric layer 303 encloses the scan line 306, the gate electrode 302a and the alignment mark 312.

Figure 4:
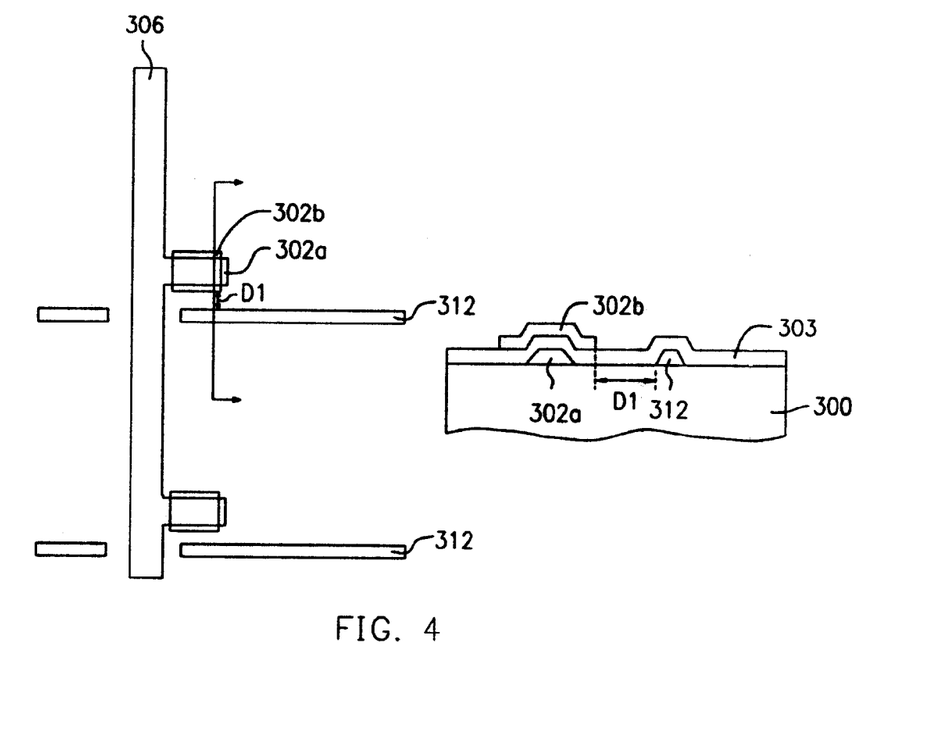

As shown in FIG. 4, a channel layer 302b is formed over the first dielectric layer 303 above the gate electrode 302a. Any mis-alignment can be determined from the relative position between the channel layer 302b and the alignment mark 312. In this embodiment, the shortest distance D1 between the channel layer 302b and the alignment mark 312 is chosen as a reference for judging alignment accuracy.

Figure 5:
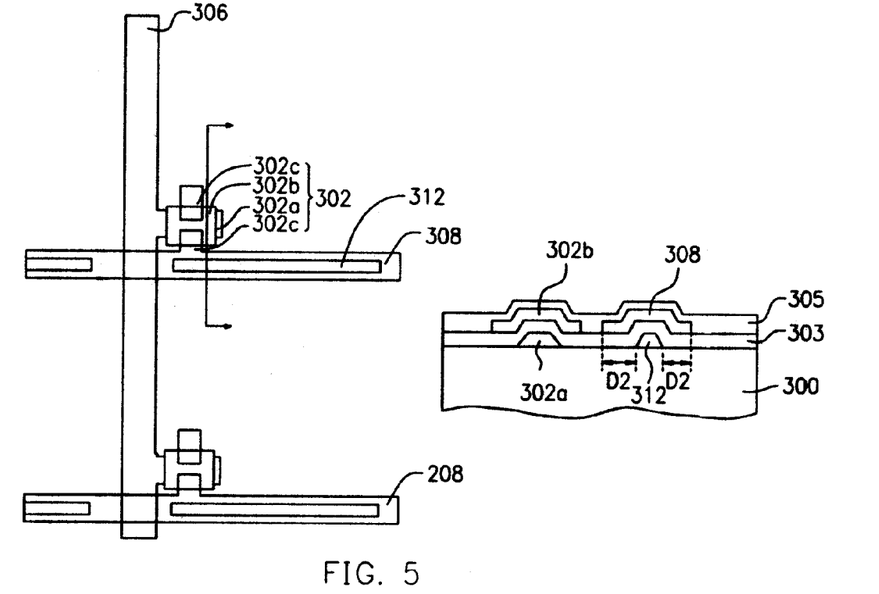

As shown in FIG. 5, a second conductive layer is formed. The second conductive layer mainly comprises of a data line 308 and a pair of source/drain terminals 302c. The gate electrode 302a, the channel layer 302b and the source/drain terminals together constitute a thin film transistor 302. After forming the second conductive layer, a second dielectric layer 305 is formed over the first dielectric layer 303. The dielectric layer 305 encloses the data line 308 and the source/drain terminals 302c.

The longitudinal alignment mark 312 is underneath the data line 308 and extends in a direction parallel to the data line 308. Position of the data line 308 and the alignment mark 312 relative to each other can be used to determine the degree of mis-alignment. For example, in this embodiment, the distance D2 from the longitudinal side of the alignment mark 312 to the edge of the data line 308 is used to determine the degree of misalignment.

Figure 6:
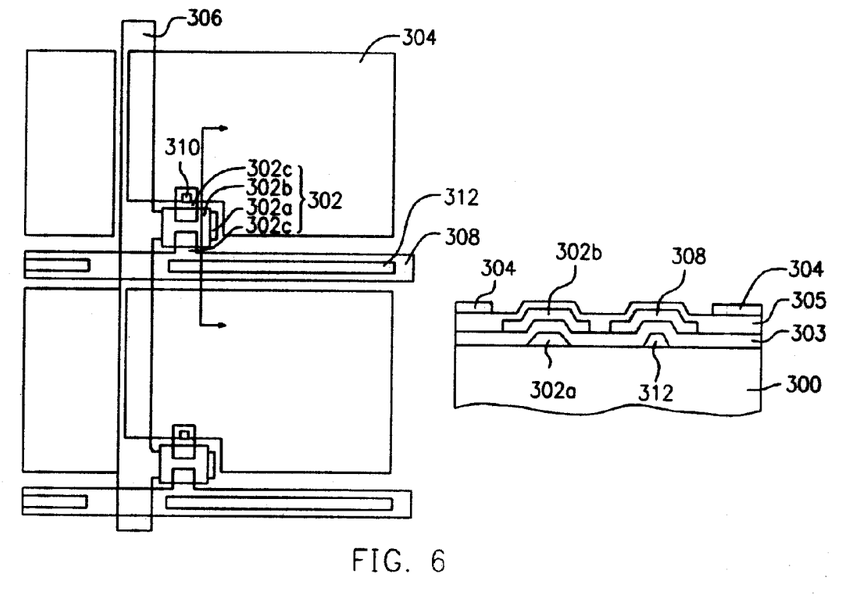

As shown in FIG. 6, a source/drain contact 310 is formed within the second dielectric layer 305. Thereafter, a pixel electrode 304 is formed over the second dielectric layer 305. Note that the pixel electrode 304 and the data line 308 are electrically connected to the respective source/drain terminals 302c.

The pixel structure as shown in FIG. 6 mainly comprises of a thin film transistor 302, a pixel electrode 304 that corresponds with the thin film transistor 302, a scan line 306, a data line 308 and an alignment mark 312. The thin film transistor 302 further comprises of the gate electrode 302a, the channel layer 302b and the source/drain terminals 302c. The scan line 306 and the gate electrode 302a of the thin film transistor 302 are electrically connected. Similarly, the pixel electrode 304 and the data line 308 are electrically connected to respective source/drain terminals 302c.

In the aforementioned fabrication process, the alignment mark 312, the gate electrode 302a and the scan line 306 are formed using the same photomask and the data line 308 and the source/drain terminals 302c are similarly formed using the same photomask. Hence, by observing the positions of the alignment mark 312 and the data line 308 relative to each other, any mis-alignment of the source/drain terminals 302c, the data line 308 relative to the gate electrode 302a, the scan line 306 can be easily found. Similarly, by observing the positions of the alignment mark 312 and the channel layer 302b relative to each other, any misalignment of the channel layer 302b relative to the gate electrode 302a, scan line 306 can also be found.

Figure 7A:
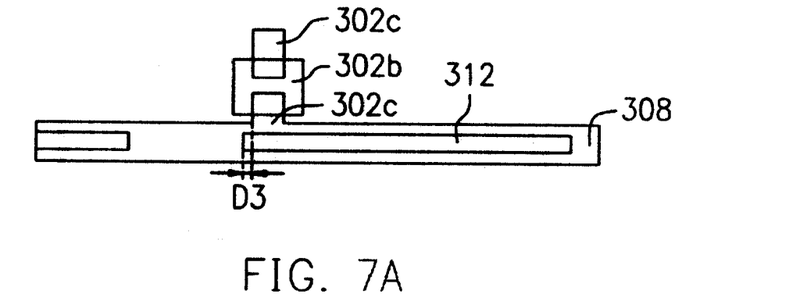
FIGS. 7A to 7D are diagrams showing various types of positional configurations between the alignment mark and the data line according to this invention.

FIGS. 7A to 7D are diagrams showing various types of positional configurations between the alignment mark and the data line according to this invention. As shown in FIG. 7A, the alignment mark 312 has a longitudinal profile. The alignment mark 312 has a width smaller than the data line 308. The alignment mark 312 is positioned directly underneath the data line 308.

Figure 7B:
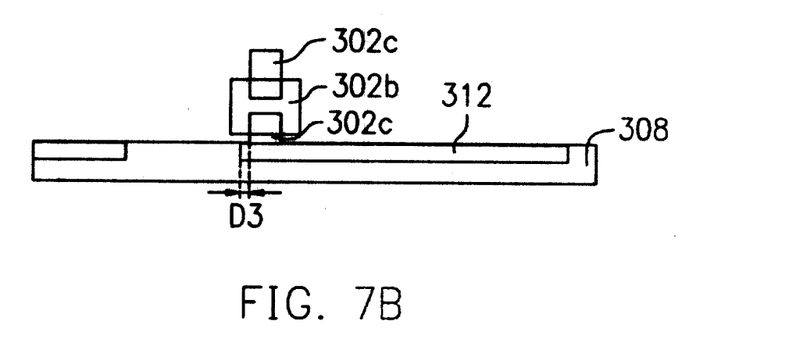
Figure 7C:
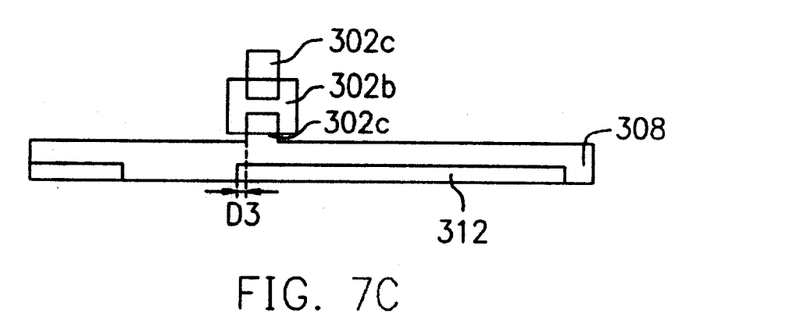

The alignment marks 312 in FIGS. 7B and 7C also have a longitudinal profile with a width smaller than the data line 308. However, the long side of the alignment mark 312 aligns with one side of the data line 308. Hence, if there is any misalignment in the X direction, the long edge of the alignment mark 312 will displace from the edge of the data line 308 by a distance so that the misalignment can be easily observed.

Figure 7D:
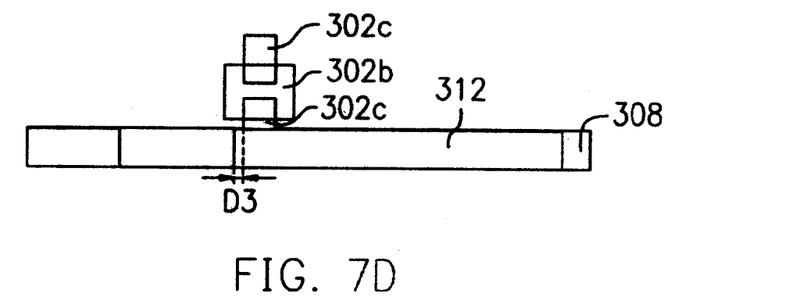

The alignment mark 312 in FIG. 7D also has a longitudinal profile. The alignment mark 312, however, has a width identical to the data line 308. Consequently, if there is any misalignment in the X direction, a portion of the alignment mark 312 will be outside the data line 308 and exposed so that the degree of misalignment can be easily determined.

In fact, the alignment 312 does not have to be in the X direction. Any misalignment in the Y direction can also be gauged. For example, in this embodiment, the distance D3 between the short side of the alignment mark 312 and the source/drain terminal 302c may also be used to determine any misalignment.

In conclusion, the pixel structure according to this invention provides at least the following benefits:

1. Only minor alteration of the photomask for patterning the gate electrode and the scan line is required to produce the alignment mark according to this invention. Hence, the steps for forming the alignment mark are fully compatible with conventional thin film transistor manufacturing process.

2. The alignment mark not only permits the determination of any non-symmetrical distribution of the source/drain terminals on each side of the channel layer, but also facilitates the finding of any positional error of the channel layer above the gate electrode.

It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims and their equivalents.

What is claimed is:

1. A pixel structure on a transparent substrate, comprising:
   a first conductive layer over the transparent substrate, wherein the first conductive layer includes a scan line, a gate electrode and an alignment mark and the gate electrode connects electrically with the scan line;
   a first dielectric layer over the transparent substrate and covering the first conductive layer;
   a channel layer over the first dielectric layer above the gate electrode;
   a second conductive layer over the first dielectric layer, wherein the second conductive layer includes a data line and a pair of source/drain terminals, the data line is above the alignment mark, and the gate electrode, the channel layer and the source/drain terminals together form a thin film transistor;
   a second dielectric layer over the first dielectric layer and covering the second conductive layer; and
   a pixel electrode over the second dielectric layer, wherein the pixel electrode and the data line are electrically connected to respective source/drain terminals.

2. The pixel structure of claim 1, wherein the scan line extends in a direction perpendicular to the data line.

3. The pixel structure of claim 1, wherein the alignment mark has a longitudinal profile.

4. The pixel structure of claim 3, wherein the alignment mark extends in a direction parallel to the data line.

5. The pixel structure of claim 3, wherein the alignment mark has a width equal to the data line.

6. The pixel structure of claim 3, wherein the alignment mark has a width smaller than the data line.

7. A thin film transistor array, comprising:
   a first conductive layer over a transparent substrate, wherein the first conductive layer includes a plurality of scan lines, a plurality of gate electrodes and a plurality of alignment marks, and each gate electrode connects electrically with a corresponding scan line;
   a first dielectric layer over the transparent substrate and covering the first conductive layer;
   a plurality of channel layers over the first dielectric layer above the respective gate electrodes;
   a second conductive layer over the first dielectric layer, wherein the second conductive layer includes a plurality of data lines and a plurality of source/drain terminals with each data line formed over a corresponding alignment mark, and the gate electrodes, the channel layers and the source/drain terminals together form the thin film transistor array;
   a second dielectric layer over the second conductive layer; and
   a plurality of pixel electrodes over the second dielectric layer, wherein each set of pixel electrode and data line connects electrically with a pair of corresponding source/drain terminals.

8. The thin film transistor array of claim 7, wherein the scan lines extend in a direction perpendicular to the data lines.

9. The thin film transistor array of claim 7, wherein the alignment marks have a longitudinal profile.

10. The thin film transistor array of claim 9, wherein the alignment marks extend in a direction parallel to the data lines.

11. The thin film transistor array of claim 9, wherein the alignment marks have a width equal to the data lines.

12. The thin film transistor array of claim 9, wherein the alignment marks have a width smaller than the data lines.

* * * * *